(12) United States Patent
Kubo et al.

(10) Patent No.: US 9,371,271 B2
(45) Date of Patent: Jun. 21, 2016

(54) METHOD FOR MANUFACTURING TERTIARY AMINO GROUP-CONTAINING LIPID

(71) Applicant: NOF CORPORATION, Tokyo (JP)

(72) Inventors: Kazuhiro Kubo, Kawasaki (JP); Kota Tange, Kawasaki (JP); Masaki Ohta, Kawasaki (JP)

(73) Assignee: NOF CORPORATION, Tokyo (JP)

( * ) Notice: Subject to any disclaimer, the term of this patent is extended or adjusted under 35 U.S.C. 154(b) by 0 days.

(21) Appl. No.: 14/412,546

(22) PCT Filed: Jun. 21, 2013

(86) PCT No.: PCT/JP2013/067045
§ 371 (c)(1),
(2) Date: Jan. 2, 2015

(87) PCT Pub. No.: WO2014/007075
PCT Pub. Date: Jan. 9, 2014

(65) Prior Publication Data
US 2015/0191416 A1     Jul. 9, 2015

(30) Foreign Application Priority Data
Jul. 2, 2012 (JP) .................. 2012-148754

(51) Int. Cl.
*C07C 213/06* (2006.01)
*C07D 295/08* (2006.01)

(52) U.S. Cl.
CPC .......... *C07C 213/06* (2013.01); *C07D 295/08* (2013.01)

(58) Field of Classification Search
CPC .................................................. C07C 213/06
See application file for complete search history.

(56) References Cited

U.S. PATENT DOCUMENTS

| | | | |
|---|---|---|---|
| 5,334,761 A * | 8/1994 | Gebeyehu et al. | ............ 564/197 |
| 2006/0008910 A1 | 1/2006 | MacLachlan et al. | |
| 2006/0083780 A1 | 4/2006 | Heyes et al. | |
| 2009/0285881 A1 | 11/2009 | Dande et al. | |
| 2011/0060032 A1 | 3/2011 | MacLachlan et al. | |
| 2011/0117125 A1 * | 5/2011 | Hope et al. | ................ 424/204.1 |
| 2011/0262527 A1 | 10/2011 | Heyes et al. | |

FOREIGN PATENT DOCUMENTS

| | | |
|---|---|---|
| CN | 101163796 A | 4/2008 |
| EP | 0 518 013 A2 | 12/1992 |
| JP | 5-155826 A | 6/1993 |
| JP | 8-509953 A | 10/1996 |
| JP | 2008-501729 A | 1/2008 |
| WO | 2005/120152 A2 | 12/2005 |
| WO | 2010/048536 A2 | 4/2010 |
| WO | 2011/000106 A1 | 1/2011 |
| WO | 2011/011447 A1 | 1/2011 |
| WO | 2011/141705 A1 | 11/2011 |

OTHER PUBLICATIONS

Search Report issued on Aug. 13, 2013 by the International Searching Authority in related application No. PCT/JP2013/067045.
Written Opinion issued on Aug. 13, 2013 by the International Searching Authority in related application No. PCT/JP2013/067045.
Wheeler, JJ et al., "Stabilized plasmid-lipid particles: construction and characterization", Gene Therapy, vol. 6, 1999, total 11 pages.
Heyes, James et al., "Cationic lipid saturation influences intracellular delivery of encapsulated nucleic acids", Journal of Controlled Release, vol. 107, Jun. 15, 2005, total 12 pages.
Communication dated Aug. 5, 2015 issued by the State Intellectual Property Office of the People's Republic of China in counterpart Chinese Application No. 201380035717.3.
Communication dated Feb. 24, 2016 issued by European Intellectual Property Office in counterpart European Patent Application No. 13813591.8.
Volynskii et al., "Preparation of diisoamyl—β—B-alkoxyethylamines", 1965 14(3), 489-91, 3 pages total, Chemical Abstracts Service, Columbus, U.S., XP-002754149.

* cited by examiner

*Primary Examiner* — Yong Chu
(74) *Attorney, Agent, or Firm* — Sughrue Mion, PLLC

(57) ABSTRACT

In production of a cationic lipid having at least one methylene group sandwiched between adjacent two cis form double bonds in the molecule, isomerization from a cis form to a trans form is suppressed.
A compound represented by the following formula (I):

$$R^1-X \quad\quad\quad (I)$$

(in Formula, $R_1$ represents a hydrocarbon group having at least one methylene group sandwiched between adjacent two cis form double bonds in the molecule and having the carbon number of 8 to 24 and X represents a releasing group) is reacted with (B) a compound having at least one of each of tertiary amino group and hydroxyl group in the molecule in a saturated hydrocarbon solvent having the carbon number of 5 to 10 in the presence of an alkali catalyst.

12 Claims, No Drawings

METHOD FOR MANUFACTURING TERTIARY AMINO GROUP-CONTAINING LIPID

CROSS REFERENCE TO RELATED APPLICATIONS

This application is a National Stage of International Application No. PCT/JP2013/067045, filed on Jun. 21, 2013, which claims priority from Japanese Patent Application No. 2012-148754, filed on Jul. 2, 2012, the contents of all which are incorporated herein by reference in their entirety.

TECHNICAL FIELD

The present invention relates to a method for manufacturing a tertiary amino group-containing lipid.

BACKGROUND ART

In recent years, gene therapy is a medical treatment which can be expected to rehabilitate and normalize, at a gene level, irregularities causing various diseases. However, the gene is very unstable. For example, in the case where the gene is administered as-is, the gene undergoes decomposition due to nuclease and the like in vivo. Therefore, selection of a vector used for gene therapy is very important.

Virus vectors used in the past are effective vectors exhibiting a high degree of gene transfer efficiency. However, cases in which clinical trials linked to death have also been reported, so that there is anxiety for the safety. Consequently, development of nonviral vectors with high safety and high gene introduction efficiency has become the mainstream and research has been performed actively all across the world.

Nonviral vectors include complexes of cationic polymers, e.g., polyethylene imine, and genes (polyplex) and complexes of liposomes made from cationic lipids and genes (lipoplex).

Most of all, the lipoplex is a vector most generally used in the present because of being functionalized easily in such a way as to have improved retentivity in blood, accumulate to a target cell, and the like depending on the type of lipid mixed and is expected greatly to go into actual use.

As for a typical example of the lipoplex, Wheeler et al. have reported that a stabilized plasmid lipid particle (SPLP) containing dioleoylphosphatidylethanolamine (DOPE) serving as a fusogenic lipid, a cationic lipid, or the like is coated with a polyethylene glycol lipid (NPL 1). In the report, as for the cationic lipid, in order to improve a drug delivery efficiency, the lipid having fusogenic properties and containing one unsaturated bond, e.g., an oleyl group, (for example, DODAC (dioleyldimethylammonium chloride)) is used.

Moreover, there is a report in which the drug delivery efficiency is further improved than ever by using a cationic lipid having at least two unsaturated bonds, e.g., a linoleyl group, and exhibiting enhanced flexibility (PTL 1). In addition, there is a report in which an analogous cationic lipid is used (PTL 2).

Regarding the cationic lipids used therein, a lipid portion and a skeleton having a cationic group are bonded with an ether group. Consequently, significant stability is exhibited because hydrolysis is not effected in contrast to the cationic lipid and the like in which a lipid portion and a skeleton having a cationic group are bonded with an ester group.

In general, in the case where such a cationic lipid including the bond with the ether group is synthesized, the method of Williamson et al. is used in which a compound having a cationic group and a hydroxyl group and a lipid compound having a leaving group are reacted in an organic solvent in the presence of a strong base at high temperatures. Examples of concrete methods for manufacturing a cationic lipid compound include production from 3-dimethylamino-1,2-propane diol containing a cationic group (dimethylamino group) and a long chain fatty bromide or a long chain fatty methane sulfonate in an aromatic solvent, e.g., benzene, toluene, or xylene, in the presence of a strong alkali catalyst, e.g., sodium hydroxide or potassium hydroxide at high temperatures, e.g., reflux (PTLs 1 and 2).

In general, it is known that a fatty acid, e.g., linoleic acid, having a methylene group sandwiched between two cis form double bonds in the molecule is oxidized easily and is isomerized easily under the conditions of high temperatures, alkali, and the like because the methylene group has high reactivity. The isomerized fatty acid (trans fatty acid) exhibits a different bioactivity. There is a report that, for example, excess intake increases the risk of decease. Therefore, an adverse effect may be exerted in the body.

Meanwhile, it is known that a fatty acid, e.g., oleic acid, having one double bond also undergoes oxidation because methylene is included on both sides of the double bond, although the reactivity is especially lower than the reactivity of the methylene group sandwiched between adjacent two cis form double bonds in the molecule of linoleic acid or the like and, therefore, isomerization does not occur easily.

CITATION LIST

Non Patent Literature

[NPL 1] Wheeler, et al., Gene Therapy 6: 271-281 (1999)

Patent Literature

[PTL 1] Japanese Unexamined Patent Application Publication (Translation of PCT Application) No. 2008-501729
[PTL 2] Japanese Unexamined Patent Application Publication (Translation of PCT Application) No. 8-509953

Technical Problem

That is, in order to obtain a cationic lipid containing a tertiary amino group through etherification of a compound, e.g., a linoleyl group, having a methylene group sandwiched between adjacent two cis form double bonds in the molecule by the method in the related art, the condition of high temperatures and strong alkali is required. Therefore, there is a problem in that a proton of the active methylene group sandwiched between cis form double bonds is withdrawn easily, isomerization from a cis form to a trans form occurs, and many isomers are contained in the objective substance.

Solution To Problem

In order to solve the above-described problems, the present inventors performed research intensively. As a result, in the production of a cationic lipid having at least one methylene group sandwiched between adjacent two cis form double bonds in the molecule, significant suppression of isomerization from the cis form to the trans form succeeded.

(1) A method for manufacturing a tertiary amino group-containing lipid, including: reacting
(A) a compound represented by Formula (I) described below $$R^1 - X \quad\quad\quad (I)$$

(in Formula, $R^1$ represents a hydrocarbon group having at least one methylene group sandwiched between adjacent two cis form double bonds in the molecule and having the carbon number of 8 to 24 and X represents a releasing group) and (B) a compound having at least one of each of tertiary amine group and hydroxyl group in the molecule in a saturated hydrocarbon solvent having the carbon number of 5 to 10 in the presence of an alkali catalyst.

(2) The above-described manufacturing method, wherein the saturated hydrocarbon solvent is hexane or methylcyclohexane.

(3) The above-described manufacturing method, wherein $R^1$ is a linoleyl group.

(4) The above-described manufacturing method, wherein the compound having at least one of each of tertiary amino group and hydroxyl group in the molecule of the item (B) is selected from the compound represented by Formula (II-1) described below

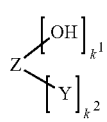

(II-1)

(In Formula, Z represents a divalent to octavalent hydrocarbon group having the carbon number of 1 to 8, which may be in a straight chain, branched, or cyclic shape, $k^1$ satisfies $1 \leq k^1 \leq 7$, $k^2$ satisfies $1 \leq k^2 \leq 3$, $2 \leq k^2 \leq 8$ is satisfied, and Y is one of functional groups represented by the following structures,

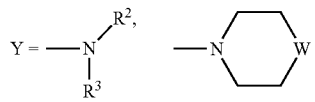

($R^2$ and $R^3$ represent independently a straight chain, branched, or cyclic hydrocarbon group having the carbon number of 1 to 8, and W represents O or $NR^4$ ($R^4$ represents an alkyl group having the carbon number of 1 to 3)) and the compound represented by Formula (II-2) described below

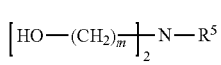

(II-2)

(in Formula, m represents 1 to 4, $R^5$ represents a straight chain or branched alkyl group having the carbon number of 1 to 4 or —$(CH_2)_n$—OH (n represents 1 to 4)).

(5) The above-described manufacturing method, wherein X is a methane sulfonate group (—$OSO_2CH_3$).

(6) The above-described manufacturing method, wherein the alkali catalyst is potassium hydroxide.

Advantageous Effects of Invention

In the case where the manufacturing method according to the present invention is used, isomerization are suppressed and, in addition, the degree of conversion of the reaction can be improved. The tertiary amino group-containing lipid, in which isomerization are suppressed as described above, has high purity. Therefore, there is an advantage in uniformity as a vector in the use as a constituent component of a nonviral vector of, for example, a lipoplex for gene introduction and, in addition, usefulness is exhibited because the possibility of exertion of an adverse effect in the body is reduced.

DESCRIPTION OF EMBODIMENTS

Regarding the compound represented by Formula (I) (hereinafter also referred to merely as "compound (A)"), $R^1$ represents a hydrocarbon group having at least one methylene group sandwiched between adjacent two cis form double bonds in the molecule and having the carbon number of 8 to 24, and is a hydrocarbon group having 2 to 6 cis form unsaturated double bonds and having the carbon number of 8 to 24. Preferably, $R^1$ is a hydrocarbon group having 1 to 4 methylene groups sandwiched between adjacent two cis form double bonds in the molecule, and more preferably a hydrocarbon group having 1 or 2 methylene groups.

As for $R^1$, usually, aliphatic hydrocarbon groups derived from fatty alcohols are used, although not limited to them. As for functional groups including a hydrocarbon group having at least one methylene group sandwiched between adjacent two cis form double bonds in the molecule and having the carbon number of 8 to 24, for example, the following groups are mentioned.

A 9,12-octadecadienyl group (linoleyl group) (abbreviated as C18:2 because 2 cis form unsaturated double bonds are included in the carbon number of 18, (1) is further added because the number of methylene group sandwiched between two cis form double bonds is 1, and hereafter abbreviation is performed in the same manner), a 10,13-nonadecadienyl group (C19:2, (1)), a 9,12,15-octadecatrienyl group (α-linolenyl group, C18:3, (2)), a 6,9,12-octadecatrienyl group (α-linolenyl group, C18:3, (2)), an 11,14-eicosadienyl group (C20:2, (1)), an 8,11,14-eicosatrienyl group (C20:3, (2)), an 11,14,17-eicosatrienyl group (C20:3, (2)), a 5,8,11,14-eicosatetraenyl group (arachidonyl group C20:4, (3)), a 5,8,11,14,17-eicosapentaenyl group (C20:5, (4)), a 7,10,13,16,19-docosapentaenyl group (C22:5, (4)), a 4,7,10,13,16,19-docosahexaenyl group (C22:6, (5)), a 13,16-docosadienyl group (C22:2, (1)), a 13,16,19-docosatrienyl group (C22:3, (2)), and a 7,10,13,16-docosatetraenyl group (C22:4, (3)) are mentioned.

Preferably, a 9,12-octadecadienyl group (linoleyl group), a 9,12,15-octadecatrienyl group (α-linolenyl group), and a 6,9,12-octadecatrienyl group (α-linolenyl group) are mentioned, and more preferably, a 9,12-octadecadienyl group (linoleyl group) is mentioned.

The symbol X represents a functional group which is released by being reacted with a hydroxyl group in the compound having at least one of each of tertiary amino group and hydroxyl group, so as to form an ether bond. Concretely, a methane sulfonate group (-OMs), a p-toluene sulfonate group (-OTs), a trifluoromethane sulfonate group (-OTf), a trifluoroethane sulfonate group (-OTresyl), chlorine, bromine, iodine, and the like are mentioned.

Preferably, a methane sulfonate group and bromine are mentioned, and more preferably, a methane sulfonate group is mentioned.

The compound which is reacted with the compound (A) (hereinafter also referred to merely as "compound (B)") is not specifically limited insofar as at least one of each of tertiary amino group and hydroxyl group is included in the molecule. Examples of preferable aspects include the compounds represented by Formulae (II-1) and (II-2).

In Formula (II-1), Z represents a divalent to octavalent hydrocarbon group having the carbon number of 1 to 8, which may be in a straight chain, branched, or cyclic shape. Preferably, Z is divalent to hexavalent, and more preferably Z is divalent or trivalent. The carbon number is preferably 1 to 6, and more preferably 1 to 3. Concretely, as for Z which is divalent, straight chain functional groups, e.g., methylene, ethylene, propylene, and butylene and cyclic functional groups, e.g., cyclohexylene and phenylene, are mentioned. As for Z which is trivalent, a hydrocarbon group derived by removing three hydroxyl groups from glycerin is mentioned. For example, as for Z which is tetravalent, a hydrocarbon group derived by removing four hydroxyl groups from erythritol is mentioned, as for Z which is pentavalent, a hydrocarbon group derived by removing five hydroxyl groups from xylitol is mentioned, and as for Z which is hexavalent, a hydrocarbon group derived by removing six hydroxyl groups from mannitol or sorbitol is mentioned. A hydrocarbon group derived by removing three hydroxyl groups from glycerin is preferable.

The symbol $k^1$ satisfies $1 \leq k^1 \leq 7$, $k^2$ satisfies $1 \leq k^2 \leq 3$, and $2 \leq k^1 + k^2 \leq 8$ is satisfied. Preferably, $k^1$ satisfies $1 \leq k^1 \leq 5$, $k^2$ is 1, and $2 \leq k^1 + k^2 \leq 6$ is satisfied. More preferably, $k^1$ is 2, $k^2$ is 1, and $k^1 + k^2 = 3$ holds.

The symbol Y is one of functional groups represented by the following structures.

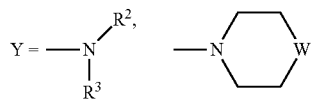

The symbols $R^2$ and $R^3$ represent independently a straight chain, branched, or cyclic hydrocarbon group having the carbon number of 1 to 8, and $R^2$ and $R^3$ may be the same or be different. Preferably, the carbon number is 1 to 4, and more preferably, the carbon number is 1 or 2. As for hydrocarbon groups, aliphatic, alicyclic, and aromatic hydrocarbon groups are mentioned. Concrete examples include a methyl group, an ethyl group, an isopropyl group, a cyclohexyl group, a phenyl group, and a benzyl group. A methyl group, an ethyl group, and an isopropyl group are preferable. A methyl group is more preferable.

The symbol W represents O or $NR^4$, and $R^4$ represents an alkyl group having the carbon number of 1 to 3. Concretely, a methyl group, an ethyl group, and a propyl group are mentioned, and a methyl group is preferable.

In Formula (II-2), m represents 1 to 4, and preferably, m is 2. The symbol $R^5$ represents a straight chain or branched alkyl group having the carbon number of 1 to 4 or $—(CH_2)_n—OH$, where n represents 1 to 4, and preferably n is 2. Concrete examples of $R^5$ include a methyl group, an ethyl group, an isopropyl group, and a hydroxyethyl group corresponding to the case where n is 2.

The amount of the compound (A) is usually 1 to 5 molar equivalents relative to one hydroxyl group of the compound (B), preferably 1 to 3 molar equivalents, further preferably 1 to 1.5 molar equivalents. In the case where the amount of the compound (A) is less than 1 molar equivalent relative to one hydroxyl group of the compound (B), the yield of an objective substance may be low because the compound (B) becomes excessive.

As for the solvent used in the reaction, saturated hydrocarbon solvents having the carbon number of 5 to 10 are mentioned. The saturated hydrocarbon solvent having the carbon number of 5 to 10 is not specifically limited and may be in a straight chain, branched, or cyclic shape. The carbon number of the saturated hydrocarbon solvent is preferably 5 to 8, and more preferably 6 to 7. Examples thereof include pentane, 2-methylbutane, cyclopentane, hexane, 2-methylpentane, 2,2-dimethylbutane, 2,3-dimethylbutane, cyclohexane, methylcyclohexane, heptane, 2-methylhexane, 3-methylhexane, 2,4-dimethylpentane, octane, isooctane, ethylcyclohexane, nonane, 2,2,5-trimethylhexane and decane. Pentane, 2-methylbutane, cyclopentane, hexane, 2-methylpentane, 2,2-dimethylbutane, 2,3-dimethylbutane, cyclohexane, methylcyclohexane, heptane, 2-methylhexane, 3-methylhexane, 2,4-dimethylpentane, octane, isooctane and ethylcyclohexane are preferable, and hexane, 2-methylpentane, 2,2-dimethylbutane, 2,3-dimethylbutane, cyclohexane, methylcyclohexane, heptane, 2-methylhexane, 3-methylhexane and 2,4-dimethylpentane are more preferable.

The amount of the solvent is not specifically limited. However, the amount is 0.1 to 100 times the amount of the compound (A) on a weight basis, preferably 0.5 to 30 times on a weight basis, and more preferably 1 to 10 times on a weight basis.

The alkali catalyst is a compound containing an alkali metal. Concrete examples include potassium hydroxide, sodium hydroxide, t-butoxy potassium, sodium hydride, potassium hydride, and metal sodium. Potassium hydroxide and sodium hydroxide are preferable, and potassium hydroxide is more preferable.

Furthermore, in order to suppress isomerization, water may be added to the solvent. In this case, the weight of water added is 0.5 to 5 parts by weight, where the weight of solvent used is specified to be 100 parts by weight, preferably 0.5 to 3 parts by weight, and more preferably 1 to 3 parts by weight.

Meanwhile, in the case where water is added to the system, a phase transfer catalyst may also be introduced in order to facilitate the reaction between an organic layer and a water layer and reduce the reaction time.

As for the phase transfer catalyst, for example, quaternary ammonium salts, crown ethers, phosphonium compounds, and chiral phase transfer catalysts may be used. Concrete examples include tetraethylammonium bromide, tetrabutylammonium hydroxide, tetrabutylammonium bromide, benzyltrimethylammonium chloride, tetraethylammonium chloride, tetrabutylammonium chloride, 18-crown-6, 15-crown-5, 12-crown-4, tetrabutylphosphonium bromide, tetramethylammonium iodide, and tetrabutylammonium iodide. Preferably, tetrabutylammonium chloride, tetrabutylammonium bromide, and tetrabutylammonium iodide are mentioned, and more preferably, tetrabutylammonium bromide is mentioned.

They may be used alone, or at least two types may be used in combination.

In the case where the phase transfer catalyst is used, the usage of the phase transfer catalyst is 0.01 to 1 molar equivalent relative to the compound (B), preferably 0.01 to 0.5 molar equivalents, and more preferably 0.01 to 0.1 molar equivalents.

Regarding the reaction between the compound (A) and the compound (B) in the saturated hydrocarbon solvent having the carbon number of 5 to 10, the temperature is 0° C. to 110° C., preferably 5° C. to 80° C., and further preferably 10° C. to 50° C. Even when the reaction temperature is low, the reaction proceeds, although the reaction may be slow. The reaction temperature can be adjusted appropriately in accordance with the boiling point of the saturated hydrocarbon solvent used.

The compound (A) has at least one methylene group sandwiched between two adjacent cis form double bonds in the molecule and, therefore, is oxidized easily and is isomerized easily. Consequently, it is preferable that the reaction and the refining are performed in an atmosphere of an inert gas, e.g., nitrogen or argon, in such a way as to avoid exposure to the air.

Regarding the treatment after the reaction, the alkali catalyst may be removed through decantation, filtration, or the like. The solution obtained by removing the alkali calalyst by these method is mixed with water, a buffer solution, and the like and, thereafter, is separated into two layers. The water layer is removed, and the organic layer is recovered, dehydrated, and concentrated, so that a tertiary amino group-containing lipid can be obtained.

Alternatively, water, the buffer solution, and the like may be added to the reaction solution containing the alkali salts without removing the alkali catalyst through decantation, filtration, or the like. In the case where the water and the buffer solution are added, heat generation accompanies and isomerization may be effected. Therefore, it is preferable that the reaction solution is cooled to 25° C. or lower and the water and the buffer solution are added gradually through, for example, dropping. After separation into the two layers, the water layer is removed, and the organic layer is recovered, dehydrated, and concentrated, so that a tertiary amino group-containing lipid can be obtained.

The resulting tertiary amino group-containing lipid is expected to contain impurities other than the objective substance. Therefore, the impurities in the resulting tertiary amino group-containing lipid may also be removed through refining by the methods described in PTLs 1 and 2, the methods described below, and the like. Regarding the refining, generally employed methods, e.g., recrystallization, crystallization, liquid-liquid extraction, and silica gel column chromatography, can be employed without limitation. In the method according to the present invention, it is preferable that impurities in the tertiary amino group-containing lipid are removed through refining by silica gel column chromatography, so as to obtain the tertiary amino group-containing lipid which is the objective substance.

The solvent used for the silica gel column chromatography is not specifically limited. For example, chloroform, methanol, hexane, ethyl acetate, water, buffers, and the like may be used alone or at least two types may be used in combination. Examples include combinations of solvents, e.g., chloroform/methanol, chloroform/methanol/water, and hexane/ethyl acetate. Chloroform/methanol and hexane/ethyl acetate are preferable and hexane/ethyl acetate is more preferable.

The usable range of the ratios of chloroform/methanol and hexane/ethyl acetate is 100/0 to 40/60 (vol/vol), and the use at 100/0 to 50/50 is preferable.

EXAMPLES

The examples according to the present invention will be described below.

Production Example 1

Synthesis of Linoleyl Methane Sulfonate

Dehydrated toluene (500 g), linoleyl alcohol (cis,cis-9,12-octadecadiene-1-ol, 100 g, 375 mmol), and triethylamine (46 g, 450 mmol) were added to a four-necked flask, and agitation was performed in a nitrogen atmosphere. After cooling to 10° C., methanesulfonyl chloride (47 g, 413 mmol) was dropped over 2 hours in such a way that the reaction temperature became 30° C. or lower. One hour from completion of dropping, the reaction solution was sampled, and disappearance of a spot of linoleyl alcohol was ascertained through TLC (chloroform development, phosphoric acid-copper sulfate color development). Ethanol (5.2 g, 113 mmol) was added, and triethylamine hydrochloric acid salts were filtrated. The filtrate was washed with ion-exchanged water (150 g), and the water layer was discarded. The same operation of washing with ion-exchanged water was performed again. The organic layer was dehydrated with anhydrous magnesium sulfate (20 g) and, thereafter, filtration and concentration were performed, so as to obtain linoleyl methane sulfonate (amount of production: 120 g, yield: 93%).

The resulting linoleyl methane sulfonate was analyzed with $^1$H-NMR (600 MHz, $CDCl_3$) and was ascertained to be an objective substance on the basis of δ 3.00 (s, 3H, $OSO_2C\underline{H}_3$), 5.42 to 5.30 (m, 4H, 2×C$\underline{H}$=C$\underline{H}$), 2.06 (q, 4H, 2×$CH_2$C$\underline{H}_2$CH=), 4.22 (t, 2H, $CH_2C\underline{H}_2OSO_2CH_3$), 2.79 (t, 2H, =CHC$\underline{H}_2$CH=), 0.89 (t, 3H, $CH_2C\underline{H}_3$).

In Examples 1 to 7 and Comparative examples 1 to 4, linoleyl methane sulfonate obtained in Production example 1 was used as a raw material, and was reacted with various substrates. Regarding samples after reaction and objective substances in each of Examples and Comparative examples, measurements were performed with $^1$H-NMR (600 MHz, $CDCl_3$).

(Method for Determining Reaction Termination Point)

A part of the reaction solution was sampled. Regarding the sampled solution, an alkali catalyst was removed by filtration with a PTFE filter (0.5 produced by ADVANTEC), and after the removal of the solvent, the measurement was performed with $^1$H-NMR (600 MHz, $CDCl_3$). The reaction was terminated at the point in time when the amount of remaining linoleyl methane sulfonate at δ 3.00 (s, 3H, $OSO_2CH_3$) derived from an methyl group of linoleyl methane sulfonate became 5.0% or less (integrated value: 0.3 or less), where the integrated value of the signal at δ 5.42 to 5.30 derived from an unsaturated bond of linoleyl group was specified to be 8H (proton).

(Method for Calculating Integrated Value of Isomer)

The integrated value of isomer was calculated from the average integrated value of signals (derived from a trans unsaturated bond) at δ 6.29, 5.94, and 5.67, where the integrated value of the signal at δ 5.42 to 5.30 derived from an unsaturated bond of linoleyl group was specified to be 8H (proton).

(Method for Calculating Degree of Conversion)

The degrees of conversion to the objective substances in Example 1, Example 2, Example 4, Example 6, Example 7, and Comparative examples 1 to 3 were calculated from the integrated value of the signal at δ 2.28 derived from a dimethylamino group (100% when 6H (proton)), where the integrated value of the signal at δ 5.42 to 5.30 derived from an unsaturated bond of linoleyl group was specified to be 8H (proton).

Likewise, the degree of conversion to the objective substance in Example 3 was calculated from the integrated value of the signal at δ 3.69 (derived from a morpholino group) (100% when 4H (proton)). The degree of conversion to the objective substance in Example 5 was calculated from the integrated value of the signal at δ 2.32 (derived from a N-methyl group) (100% when 3H (proton)).

Example 1

Synthesis of 1,2-dilinoleyloxy-N,N-dimethylaminopropane (DLinDMA)

Hexane (30 ml) and potassium hydroxide (3.1 g, 54.4 mmol) were added to a screw tube, and 3-(dimethylamino)-

1,2-propanediol (0.72 g, 6.04 mmol: DAP) was dropped in a nitrogen atmosphere under agitation. Thereafter, linoleyl methane sulfonate (5.0 g, 14.5 mmol) obtained in Production example 1 was dropped, and agitation was performed at room temperature. After 48 hours, the reaction was terminated because remaining linoleyl methane sulfonate became 0.9% (degree of conversion: 65.0%, integrated value of isomer: 0.017).

The reaction solution was subjected to decantation, and a supernatant solution was added to a phosphoric acid buffer (75 ml) with a pH of 6, followed by agitation. After standing to separate into layers, a water layer was discarded. Acetonitrile (20 ml) was added. After agitation and standing, a lower layer (acetonitrile layer) was removed. Acetonitrile (20 ml) was added once again and the same operation was performed again. A hexane layer was dehydrated with magnesium sulfate (1.0 g) and was filtrated. Subsequently, solvent was removed, so as to obtain a roughly refined product (3.3 g). This was refined with a silica gel (DAISOGEL IR-60-25/40) column by using a hexane solution containing 5 to 20 percent by volume of ethyl acetate, so that an objective substance (2.0 g) was obtained (integrated value of isomer: 0.015).

The resulting objective substance was analyzed with $^1$H-NMR (600 MHz, CDCl$_3$) and was ascertained to be the objective substance on the basis of $^1$H-NMR (600 MHz, CDCl$_3$): δ 5.42 to 5.30 (m, 8H, 4×C$\underline{H}$=C$\underline{H}$), 3.59 to 3.44 (m, 7H, OC$\underline{H}$, 3×OC$\underline{H}_2$), 2.79 (t, 4H, 2×=CHC$\underline{H}_2$CH=), 2.40 (m, 2H, NC$\underline{H}_2$), 2.28 (s, 6H, 2×NC$\underline{H}_3$), 2.06 (q, 8H, 4×CH$_2$C$\underline{H}_2$CH=), 1.56 (m, 4H, 2×C$\underline{H}_2$CH$_2$O), 1.41 to 1.28 (m, 32H), 0.89 (t, 6H, 2×CH$_2$C$\underline{H}_3$).

Furthermore, it was ascertained that the same signal as the signal of the same compound described in PTL 1 was obtained.

The experiment in Comparative example 1 will be described below.

Comparative Example 1

Synthesis of
1,2-dilinoleyloxy-N,N-dimethylaminopropane
(DLinDMA)

Dehydrated toluene (30 ml) and 60% sodium hydride (1.2 g, 30.0 mmol) were added to a four-necked flask, and DAP (0.57 g, 4.84 mmol) was dropped under agitation in a nitrogen atmosphere. Thereafter, linoleyl methane sulfonate (5.0 g, 14.5 mmol) was dropped, and agitation was performed at 110° C. for 3 hours (degree of conversion: 59.0%, integrated value of isomer: 0.073). After cooling to room temperature, cooling with ice was performed, and ethanol (3 mL) was added to the reaction solution gradually. Furthermore, dilution was performed with 150 ml of toluene and, subsequently, washing was performed with distilled water (150 mL x 2 times) and saturated saline solution (150 mL). Magnesium sulfate (1.0 g) was added to the organic layer to dehydrate and, thereafter, filtration and removal of the solvent were performed, so as to obtain a roughly refined product. The roughly refined product was refined with a silica gel (DAISOGEL IR-60-25/40) column chromatography by using a chloroform solution containing 0% to 5% of methanol, so that an objective substance (1.6 g) was obtained (integrated value of isomer: 0.071).

The results of the integrated value of isomer regarding Example 1 and Comparative example 1 are shown in Table 1.

TABLE 1

| Change in integrated value of isomer | | |
|---|---|---|
|  | After reaction | After column refining |
| Example 1 | 0.017 | 0.015 |
| Comparative example 1 | 0.073 | 0.071 |

As is shown in Table 1, regarding Example 1 in which hexane was used as the reaction solution, the integrated value of isomer after the reaction was suppressed significantly as compared with the integrated value of Comparative example 1 in which toluene was used.

Meanwhile, regarding the column refining thereafter, the integrated value of isomer was reduced and it was made clear that the isomer was not removed completely, although the isomer was removed slightly. That is, it was found that the isomer content in the objective substance was influenced by the isomer content in the reaction.

Then, regarding Examples 2 to 7 and Comparative examples 2 to 4 described below, comparisons were made on the basis of the integrated value of isomer after the reaction.

Example 2

Synthesis of
1,2-dilinoleyloxy-N,N-dimethylaminopropane
(DLinDMA)

In a nitrogen atmosphere, hexane (30 mL), potassium hydroxide (3.1 g, 54.4 mmol), and water (0.6 g: 3 parts by weight relative to 100 parts by weight of hexane) were added to a four-necked flask, and 3-(dimethylamino)-1,2-propanediol (0.72 g, 6.04 mmol: DAP) was dropped under agitation. Thereafter, linoleyl methane sulfonate (5.0 g, 14.5 mmol) was added, and agitation was performed at 40° C. for 19 hours. The reaction was terminated because remaining linoleyl methane sulfonate became 1.0% (degree of conversion: 64.0%, integrated value of isomer: 0.009).

Example 3

Synthesis of 1,2-dilinoleyloxy-morpholinopropane

In a nitrogen atmosphere, hexane (30 mL) and potassium hydroxide (3.1 g, 54.4 mmol) were added to a four-necked flask, and 3-morpholino-1,2-propanediol (0.98 g, 6.1 mmol: MPP) was dropped under agitation. Thereafter, linoleyl methane sulfonate (5.0 g, 14.5 mmol) was added, and agitation was performed at room temperature for 23 hours. The reaction was terminated because linoleyl methane sulfonate disappeared (degree of conversion: 72.3%, integrated value of isomer: 0.012).

Example 4

Synthesis of
1,2-dilinoleyloxy-N,N-dimethylaminopropane
(DLinDMA)

In a nitrogen atmosphere, methylcyclohexane (30 mL) and potassium hydroxide (3.1 g, 54.4 mmol) were added to a four-necked flask, and 3-(dimethylamino)-1,2-propanediol (0.72 g, 6.04 mmol: DAP) was dropped under agitation. Thereafter, linoleyl methane sulfonate (5.0 g, 14.5 mmol) was added, and agitation was performed at 40° C. for 13 hours. The reaction was terminated because remaining linoleyl methane sulfonate became 2.1% (degree of conversion: 68.0%, integrated value of isomer: 0.024).

Example 5

Synthesis of N,N-dilinoleyloxyethyl-N-methylamine

In a nitrogen atmosphere, hexane (30 mL) and potassium hydroxide (3.1 g, 54.4 mmol) were added to a four-necked flask, and N-methyldiethanolamine (0.72 g, 6.04 mmol: MDA) was dropped under agitation. Thereafter, linoleyl methane sulfonate (5.0 g, 14.5 mmol) was added, and agitation was performed at room temperature for 5 hours. The reaction was terminated because remaining linoleyl methane sulfonate became 3.9% (degree of conversion: 87.0%, integrated value of isomer: 0.011).

Example 6

Synthesis of
1,2-dilinoleyloxy-N,N-dimethylaminopropane
(DLinDMA)

In a nitrogen atmosphere, hexane (30 mL), potassium hydroxide (3.1 g, 54.4 mmol), water (0.6 g: 3 parts by weight relative to 100 parts by weight of hexane), and tetrabutylammonium bromide (0.04 g, 0.12 mmol: TBAB) were put into a four-necked flask, and 3-(dimethylamino)-1,2-propanediol (0.72 g, 6.04 mmol: DAP) was dropped under agitation. Thereafter, linoleyl methane sulfonate (5.0 g, 14.5 mmol) was added, and agitation was performed at room temperature for 11 hours. The reaction was terminated because remaining linoleyl methane sulfonate became 0.9% (degree of conversion: 65.0%, integrated value of isomer: 0.011).

Example 7

Synthesis of
1,2-dilinoleyloxy-N,N-dimethylaminopropane
(DLinDMA)

In a nitrogen atmosphere, hexane (30 mL) and potassium hydroxide (6.1 g, 108.7 mmol) were put into a four-necked flask, and 3-(dimethylamino)-1,2-propanediol (0.72 g, 6.04 mmol: DAP) was dropped under agitation. Thereafter, linoleyl methane sulfonate (5.0 g, 14.5 mmol) was added, and agitation was performed at room temperature for 3 hours. The reaction was terminated because remaining linoleyl methane sulfonate became 0.2% (degree of conversion: 59.2%, integrated value of isomer: 0.027).

Comparative Example 2

Synthesis of
1,2-dilinoleyloxy-N,N-dimethylaminopropane
(DLinDMA)

In a nitrogen atmosphere, dehydrated toluene (30 ml) and potassium hydroxide (1.8 g, 28.8 mmol) were added to a four-necked flask, and 3-(dimethylamino)-1,2-propanediol (0.57 g, 4.78 mmol) was dropped under agitation. Thereafter, linoleyl methane sulfonate (5.0 g, 14.5 mmol) was added, and refluxing was performed at 110° C. for 3 hours. The reaction was terminated because remaining linoleyl methane sulfonate became 4.8% (degree of conversion: 51.1%, integrated value of isomer: 0.142).

Comparative Example 3

Synthesis of
1,2-dilinoleyloxy-N,N-dimethylaminopropane
(DLinDMA)

In a nitrogen atmosphere, dehydrated toluene (30 ml) and potassium hydroxide (4.9 g, 87.0 mmol) were added to a four-necked flask, and 3-(dimethylamino)-1,2-propanediol (0.57 g, 4.78 mmol: DAP) was dropped under agitation. Thereafter, linoleyl methane sulfonate (5.0 g, 14.5 mmol) was added, and reaction was effected at room temperature for 14.5 hours. The reaction was terminated because isomers increased to 0.079%, although remaining linoleyl methane sulfonate was 51.1% and, therefore, 5.0% or less was not satisfied (degree of conversion: 28.9%, integrated value of isomer: 0.079).

Comparative Example 4

Synthesis of N,N-dilinoleyloxyethyl-N-methylamine

In a nitrogen atmosphere, dehydrated toluene (30 ml) and potassium hydroxide (3.1 g, 54.4 mmol) were added to a four-necked flask, and N-methyldiethanolamine (0.72 g, 6.04 mmol: MDA) was dropped under agitation. Thereafter, linoleyl methane sulfonate (5.0 g, 14.5 mmol) was added, and reaction was effected at room temperature for 44 hours. The reaction was terminated because remaining linoleyl methane sulfonate became 3.5% (degree of conversion: 39.5%, integrated value of isomer: 0.042).

TABLE 2

| | | | | | | | | Average |
|---|---|---|---|---|---|---|---|---|
| | | | | | | | | integrated |
| | | | | | Equivalent | | | Degree of | value |
| | Substrate | Solvent | Catalyst | amount | Temperature | Time | conversion | of isomer |
| Example 1 | DAP | hexane | KOH | 9 eq | room temperature | 48 h | 65.0% | 0.017 |
| Example 2 | DAP | hexane + water | KOH | 9 eq | 40° C. | 19 h | 64.0% | 0.009 |
| Example 3 | MPP | hexane | KOH | 9 eq | room temperature | 23 h | 72.3% | 0.012 |
| Example 4 | DAP | methylcyclohexane | KOH | 9 eq | 40° C. | 13 h | 68.0% | 0.024 |
| Example 5 | MDA | hexane | KOH | 9 eq | room temperature | 5 h | 87.0% | 0.011 |

Integrated value of isomer after reaction

TABLE 2-continued

Integrated value of isomer after reaction

| | Substrate | Solvent | Catalyst | Equivalent amount | Temperature | Time | Degree of conversion | Average integrated value of isomer |
|---|---|---|---|---|---|---|---|---|
| Example 6 | DAP | hexane + water | KOH + TBAB | 9 eq | room temperature | 11 h | 65.0% | 0.011 |
| Example 7 | DAP | hexane | KOH | 18 eq | room temperature | 3 h | 59.2% | 0.027 |

TABLE 3

Integrated value of isomer after reaction

| | Substrate | Solvent | Catalyst | Equivalent amount | Temperature | Time | Degree of conversion | Average integrated value of isomer |
|---|---|---|---|---|---|---|---|---|
| Comparative example 1 | DAP | toluene | NaH | 6 eq | 110° C. | 3 h | 59.0% | 0.073 |
| Comparative example 2 | DAP | toluene | KOH | 6 eq | 110° C. | 3 h | 51.1% | 0.142 |
| Comparative example 3 | DAP | toluene | KOH | 18 eq | room temperature | 14.5 h | 28.9% | 0.079 |
| Comparative example 4 | MDA | toluene | KOH | 9 eq | room temperature | 44 h | 39.5% | 0.042 |

The case where the compound having at least one of each of tertiary amino group and hydroxyl group is 3-(dimethylamino)-1,2-propanediol (DAP) corresponds to Examples 1, 2, 4, 6, and 7 and Comparative examples 1, 2, and 3. When the integrated values of isomer of them are compared, the integrated values of isomer in Examples were 0.009 to 0.027, whereas those in Comparative examples were 0.073 to 0.142. Therefore, regarding Examples, isomerization was able to be suppressed and, in addition, the degrees of conversion were able to be increased.

Likewise, in Examples 3 and 5, 3-morpholino-1,2-propanediol (MPP) and N-methyldiethanolamine (MDA), respectively, were used instead of DAP, and it was found that the integrated values of isomer were 0.012 and 0.011 and, therefore, isomerization was suppressed as with the case of 3-(dimethylamino)-1,2-propanediol (DAP).

According to comparisons between the cases where MDA was used, the integrated value of isomer of Comparative example 4 was 0.042, whereas regarding Example 5, the integrated value of isomer was 0.011 and, therefore, isomerization was able to be suppressed and the degree of conversion were able to be increased.

It was found that regarding Example 6 in which water and tetrabutylammonium bromide (TBAB) were used in the reaction system, the reaction time was able to be reduced as compared with Example 2 in which the same substrate, solvent, and water were used.

While the invention has been described in detail and with reference to specific embodiments thereof, it will be apparent to one skilled in the art that various changes and modifications can be made therein without departing from the spirit and scope thereof.

The present application is based on Japanese Patent Application filed on Jul. 2, 2012 (Japanese Patent Application No. 2012-148754), and all of its contents are incorporated herein by reference. Also, all the references cited herein are incorporated as a whole.

The invention claimed is:

1. A method for manufacturing a tertiary amino group-containing lipid, comprising:
   reacting
   (A) a compound represented by Formula (I) described below $$R^1-X \quad (I)$$

in Formula, $R^1$ represents a hydrocarbon group having at least one methylene group sandwiched between adjacent two cis form double bonds in the molecule and having the carbon number of 8 to 24 and X represents a functional group which is released by reaction with a hydroxyl group in the compound having at least one of each of tertiary amino groups and hydroxyl group, so as to form an ether bond and (B) a compound having at least one of each of tertiary amino group and hydroxyl group in the molecule in a saturated hydrocarbon solvent having a carbon number of 5 to 10 in the presence of an alkali catalyst,
   wherein the compound having at least one of each of tertiary amino group and hydroxyl group in the molecule of the item (B) is selected from the compound represented by Formula (II-1) described below

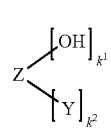
   (II-1)

in Formula, Z represents a divalent to octavalent hydrocarbon group having the carbon number of 1 to 8, which may be in a straight chain, branched, or cyclic shape, $k^1$ satisfies $1 \leq k^1 \leq 7$, $k^2$ satisfies $1 \leq k^2 \leq 3$, $2 \leq k^1 + k^2 \leq 8$ is satisfied, and Y is one of functional groups represented by the following structures,

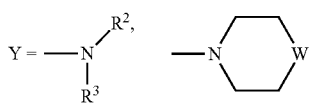

$R^2$ and $R^3$ represent independently a straight chain, branched, or cyclic hydrocarbon group having the carbon number of 1 to 8, and W represents O or $NR^4$; $R^4$ represents an alkyl group having the carbon number of 1 to 3 and the compound represented by Formula (II-2) described below

(II-2)

in Formula, m represents 1 to 4, $R^5$ represents a straight chain or branched alkyl group having the carbon number of 1 to 4 or —$(CH_2)_n$—OH; and n represents 1 to 4.

2. The method according to claim 1, wherein the saturated hydrocarbon solvent is hexane or methylcyclohexane.

3. The method according to claim 1, wherein $R^1$ is a linoleyl group.

4. The method according to claim 2, wherein $R^1$ is a linoleyl group.

5. The method according to claim 1, wherein X is a methane sulfonate group (—$OSO_2CH_3$).

6. The method according to claim 2, wherein X is a methane sulfonate group (—$OSO_2CH_3$).

7. The method according to claim 3, wherein X is a methane sulfonate group (—$OSO_2CH_3$).

8. The method according to claim 4, wherein X is a methane sulfonate group (—$OSO_2CH_3$).

9. The method according to claim 1, wherein the alkali catalyst is potassium hydroxide.

10. The method according to claim 2, wherein the alkali catalyst is potassium hydroxide.

11. The method according to claim 3, wherein the alkali catalyst is potassium hydroxide.

12. The method according to claim 4, wherein the alkali catalyst is potassium hydroxide.

* * * * *